US006948501B2

(12) United States Patent
Rastegar et al.

(10) Patent No.: US 6,948,501 B2
(45) Date of Patent: Sep. 27, 2005

(54) PATIENT SUPPORT FOR EXTERNAL COUNTERPULSATION CARDIAC ASSIST DEVICE

(75) Inventors: Jahangir S. Rastegar, Stony Brook, NY (US); Harry Soroff, Northport, NY (US)

(73) Assignee: P.P.T.T. L.L.P., Northport, NY (US)

( * ) Notice: Subject to any disclaimer, the term of this patent is extended or adjusted under 35 U.S.C. 154(b) by 373 days.

(21) Appl. No.: 10/135,063

(22) Filed: Apr. 29, 2002

(65) Prior Publication Data

US 2003/0200971 A1 Oct. 30, 2003

(51) Int. Cl.[7] ........................ A61G 15/00; A61F 13/00; A61B 19/00; A61B 5/37

(52) U.S. Cl. ....................... 128/845; 128/846; 128/869; 128/870; 606/242; 601/152

(58) Field of Search ................................ 128/845, 846, 128/869, 870; 606/242; 601/152

(56) References Cited

U.S. PATENT DOCUMENTS 1,089,801 A * 3/1914 Swanson ..................... 602/15
3,612,042 A * 10/1971 Fry ............................. 601/24
4,202,355 A * 5/1980 Loeffler ...................... 600/587
4,526,355 A * 7/1985 Moore et al. .................. 5/624
4,579,324 A * 4/1986 McConnell .................... 5/618
4,602,618 A * 7/1986 Berze ......................... 601/24
4,621,625 A * 11/1986 Powlan Roy Y. ............. 602/33
4,674,495 A * 6/1987 Orr ....................... 128/207.14
4,702,465 A * 10/1987 McConnell .................... 5/646
4,715,361 A * 12/1987 Mauldin et al. ............ 601/101
4,911,152 A * 3/1990 Barnes et al. ................. 602/23
4,974,830 A * 12/1990 Genovese et al. ............ 601/29
5,048,825 A * 9/1991 Kelly ......................... 482/94
5,063,918 A * 11/1991 Guhl ........................... 602/40
5,239,987 A * 8/1993 Kaiser et al. ................. 601/34
5,290,219 A * 3/1994 Hetrick ........................ 602/32
5,333,604 A * 8/1994 Green et al. .................. 601/33
5,401,236 A * 3/1995 Summerville ................ 602/33
5,509,894 A * 4/1996 Mason et al. ................. 601/34
5,735,806 A * 4/1998 Leibovic ...................... 602/32
5,800,366 A * 9/1998 Bertrand ...................... 601/24
5,901,581 A * 5/1999 Chen et al. ................... 601/34
5,961,512 A * 10/1999 Purnell .......................... 606/1
6,076,525 A * 6/2000 Hoffman ..................... 128/845
6,428,497 B1 * 8/2002 Crouch ........................ 602/32
6,629,944 B2 * 10/2003 Smart .......................... 602/36
6,685,658 B1 * 2/2004 Dietz et al. .................... 601/5
6,726,642 B2 * 4/2004 Danielsson et al. ............ 602/5
6,821,288 B2 * 11/2004 Schaeffer .................... 606/240

* cited by examiner

*Primary Examiner*—Henry Bennett
*Assistant Examiner*—Nihir Patel
(74) *Attorney, Agent, or Firm*—Scully, Scott, Murphy & Presser

(57) ABSTRACT

A patient support for an external counterpulsation cardiac assist procedure. The patient support includes: a base; and at least one support connected to the base for maintaining at least a portion of the patient above a tabletop during a positive pressure portion of the external counterpulsation cardiac assist procedure. In one embodiment, the base is a tabletop and the at least one support is movably supported on the table top in lateral and/or vertical directions. In another embodiment, the base is higher than the tabletop and the at least one support is a sling.

23 Claims, 7 Drawing Sheets

PATIENT SUPPORT FOR EXTERNAL COUNTERPULSATION CARDIAC ASSIST DEVICE

BACKGROUND OF THE INVENTION

1. Field of the Invention

The present invention relates generally to external counterpulsation cardiac assist, and more particularly, to a patient support for use with external counterpulsation cardiac assist.

2. Prior Art

In external counterpulsation cardiac assist device (APPLICATOR) applicators (hereinafter "applicator") of the prior art, the limb pressure is generated by inflating balloon-like chambers that surround the limb. In addition, to keep the volume of the inflow air in check, the balloon-like chambers are encased in a relatively inextensible fabric to minimize the bulging out of the applicator assembly. A cross-section of a typical such arrangement is illustrated in FIG. 1.

The applicator 100 (alternatively referred to as an actuator) is used by laying the patient on a bed, "wrapping" the applicator around a limb or other body portion 101 (such as the legs, thighs, arms, or buttocks) and affixing the outer liner 104 by Velcro or other similar means such that the assembly stays tightly over the limb 101. The applicators are generally constructed with an inner layer 102 and a relatively inextensible outer layer 104. Between the inner and outer layers 102 and 104, balloon-like members 106 are positioned. The balloon like members 106 are typically made from an elastic material and provide inner cavities or chambers. The applicator operates by pressurizing the balloon-like members 106 with air or other gases through an inlet and/or outlet 108, preferably in synchronization with the patient's cardiac cycle.

Part of the limb 101 such as ankles, knees, feet, elbows, chest area, neck and the head are not covered since due to the absence of a considerable amount of muscle mass, no significant amount of blood can be displaced by the external pressure by the applicators. In the applicators of the prior art, the patient's leg, thighs, arms and buttock are supported by the outer layer 104 over the bed or table (collectively referred to herein as a tabletop). As the result, as the air pressure builds up in the chamber 106, the outer layer 104 has a tendency to bulge out, thereby lifting the limb 100 above the top surface of the tabletop. This is the case even though relatively inextensible outer applicator layers are commonly used which make them resist radial extension but cannot prevent longitudinal bulging of the applicators. The aforementioned lifting following the pressurization of the applicator is illustrated in FIGS. 2*a* and 2*b*. FIG. 2*a* illustrates the applicator during an evacuation cycle in which the chamber 106 is evacuated and FIG. 2*b* illustrates a pressurization cycle on the right in which the chamber 106 is pressurized with air or any other suitable gas. As can be readily appreciated from the comparison between FIGS. 2*a* and 2*b*, the pressurization of the chamber 106 results in a lifting of the limb 100 by an amount H.

Appreciating that the applicator can operate at up to one cycle per heart beat cycle, i.e., in the order of about 60–80 times a minute, and that each time the patient's limb(s) 101 is effectively thrown up a considerable distance (H) above the top surface 112 of the tabletop 110, the discomfort facing the patient becomes apparent. In fact, the length of time that the procedure can be continued is very much related to how long the patient can tolerate such highly stressful and rapid lifting, without excessive and harmful fatigue. In addition, patients also tend to tighten their muscles due to such rapid lifting, thereby reducing the effectiveness of the entire procedure.

A need therefore exists for means to alleviate patients from the stress and other harmful effects of the aforementioned lifting actions during the procedure.

SUMMARY OF THE INVENTION

Therefore it is an object of the present invention to provide a patient support for maintaining at least a portion of the patient above a tabletop during a positive pressure portion of the external counterpulsation cardiac assist procedure.

Accordingly, a patient support for external counterpulsation cardiac assist devices is provided. The patient support comprises: a base; and at least one support connected to the base for maintaining at least a portion of the patient above a tabletop during a positive pressure portion of the external counterpulsation cardiac assist procedure.

Preferably, the at least one support comprises a padded portion fabricated of a soft material. The at least one support further preferably comprises a fixing means for fixing the at least a portion of the patient thereto. Preferably, the fixing means comprises a strap having a first end fixed to the at least one support and a corresponding buckle fixed to the at least one support.

In a first embodiment of the patient support, the base is the tabletop. In which case, the patient support preferably further comprises moving means for movably fixing the at least one support to the tabletop such that the at least one support can be movably positioned under the portion of the patient to be maintained above the tabletop. The moving means preferably comprises the at least one support having a slide portion which is slidably arranged in a corresponding slot on a top surface of the tabletop. Preferably, the at least one support further has a locking means for locking the at least one support at a predetermined position corresponding to the portion of the patient to be maintained above the tabletop. Preferably, the locking means comprises a locking shaft having a keyed portion on one end and a threaded portion on another end, the keyed portion being slidingly disposed in a corresponding keyway in the tabletop, the locking means further comprising a threaded knob threadingly engaged with the threaded portion, wherein tightening of the knob on the shaft causes the keyed portion to engage a lower surface of the tabletop to thereby lock the at least one support thereon.

Where the base is a tabletop, the patient support preferably further comprises height adjustment means for movably fixing the at least one support to the tabletop such that a height of the at least one support above the tabletop can be adjusted. Preferably, the height adjustment means comprises at least one rod connected to the at least one support, the at least one rod being slidingly disposed in a corresponding bore in the tabletop. Preferably, the patient support further comprises a locking means for locking the rod at a predetermined height. The locking means preferably comprises the at least one rod having at least one groove and a detent housed in the tabletop for operatively engaging with the at least one groove.

The patient support preferably further comprises biasing means for biasing the at least one support above the tabletop. The biasing means preferably comprises a constant tension spring corresponding to each of the at least one supports, the constant tension spring having a portion disposed in the tabletop and a portion connected to the at least one support.

In a second embodiment of the patient support, the base is raised above the level of the patient and tabletop. In such an embodiment, the at least one support preferably comprises a sling, the sling having a tensioning member and balancing means for maintaining the sling in a balanced position to maintain the at least a portion of the patient above the tabletop. Preferably, the tensioning member is a cable attached at a first end to the sling and at a second end to the balancing means. The balancing means is preferably a constant tension spring attached to the second end. Alternatively, the balancing means is a counterweight attached to the second end.

Also provided is a patient table for use with external counterpulsation cardiac assist. The patient table comprises: a tabletop having a top surface; and at least one support connected to the tabletop for maintaining at least a portion of the patient above the top surface of the tabletop during a positive pressure portion of the external counterpulsation cardiac assist procedure.

The at least one support preferably comprises a padded portion fabricated of a soft material. Preferably, the at least one support further comprises a fixing means for fixing the at least a portion of the patient thereto. The fixing means preferably comprises a strap having a first end fixed to the at least one support and a corresponding buckle fixed to the at least one support.

The patient table preferably further comprises moving means for movably fixing the at least one support to the tabletop such that the at least one support can be movably positioned under the portion of the patient to be maintained above the tabletop. The moving means preferably comprises the at least one support having a slide portion which is slidably arranged in a corresponding slot on the top surface of the tabletop. Preferably the at least one support further has a locking means for locking the at least one support at a predetermined position corresponding to the portion of the patient to be maintained above the tabletop. Preferably, the locking means comprises a locking shaft having a keyed portion on one end and a threaded portion on another end, the keyed portion being slidingly disposed in a corresponding keyway in the tabletop, the locking means further comprising a threaded knob threadingly engaged with the threaded portion, wherein tightening of the knob on the shaft causes the keyed portion to engage a lower surface of the tabletop to thereby lock the at least one support thereon.

The patient table further comprising height adjustment means for movably fixing the at least one support to the tabletop such that a height of the at least one support above the tabletop can be adjusted. The height adjustment means preferably comprises at least one rod connected to the at least one support, the at least one rod being slidingly disposed in a corresponding bore in the tabletop. The patient table preferably further comprises a locking means for locking the rod at a predetermined height, wherein the locking means comprises the at least one rod having at least one groove and a detent housed in the tabletop for operatively engaging with the at least one groove.

The patient table preferably further comprises biasing means for biasing the at least one support above the top surface of the tabletop. Preferably, the biasing means comprises a constant tension spring corresponding to each of the at least one supports, the constant tension spring having a portion disposed in the tabletop and a portion connected to the at least one support.

Still yet provided is a method for supporting a patient during external counterpulsation cardiac assist. The method comprising: applying at least a positive pressure cycle to at least a portion of the patient; and supporting the at least a portion of the patient above a tabletop during the positive pressure portion of the external counterpulsation cardiac assist procedure.

The method preferably further comprising movably fixing at least one support to the tabletop such that the at least one support can be movably positioned under the portion of the patient to be maintained above the tabletop. The method preferably further comprising locking the at least one support at a predetermined position corresponding to the portion of the patient to be maintained above the tabletop.

The method preferably further comprising movably fixing at least one support to the tabletop such that a height of the at least one support above the tabletop can be adjusted.

BRIEF DESCRIPTION OF THE DRAWINGS

These and other features aspects, and advantages of the apparatus and methods of the present invention will become better understood with regard to the following description, appended claims, and accompanying drawings where:

DETAILED DESCRIPTION OF THE PREFERRED EMBODIMENT

Figure 1:
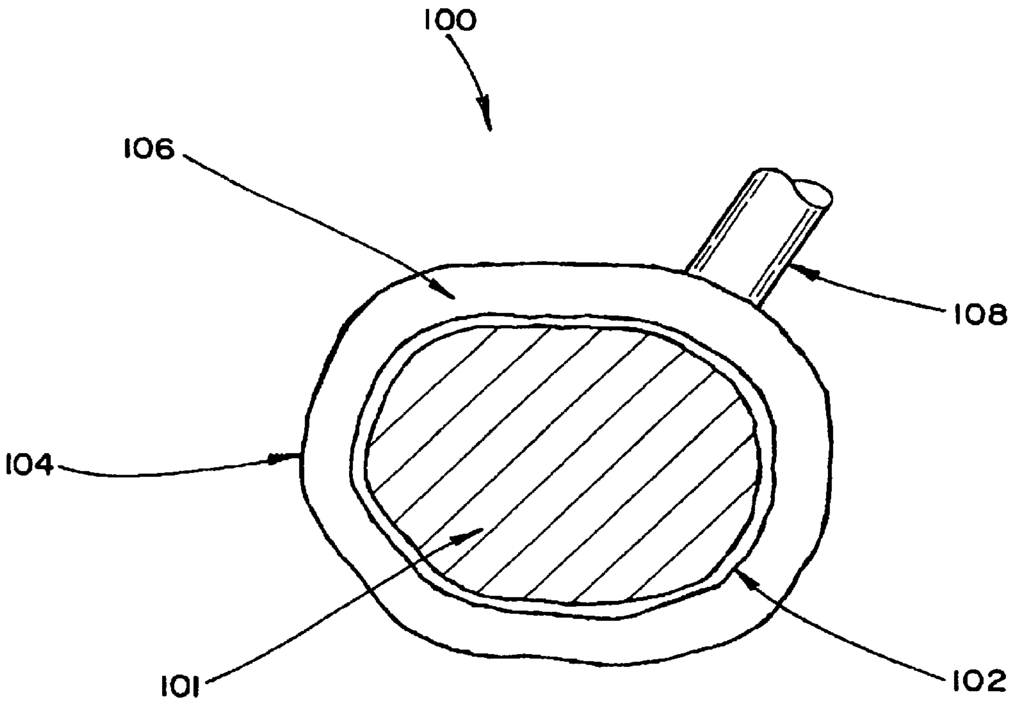
FIG. 1 (PRIOR ART)
FIG. 1 illustrates a section al view of an APPLICATOR of the prior art shown disposed about a patient's limb.
Figures 2A, 2B:
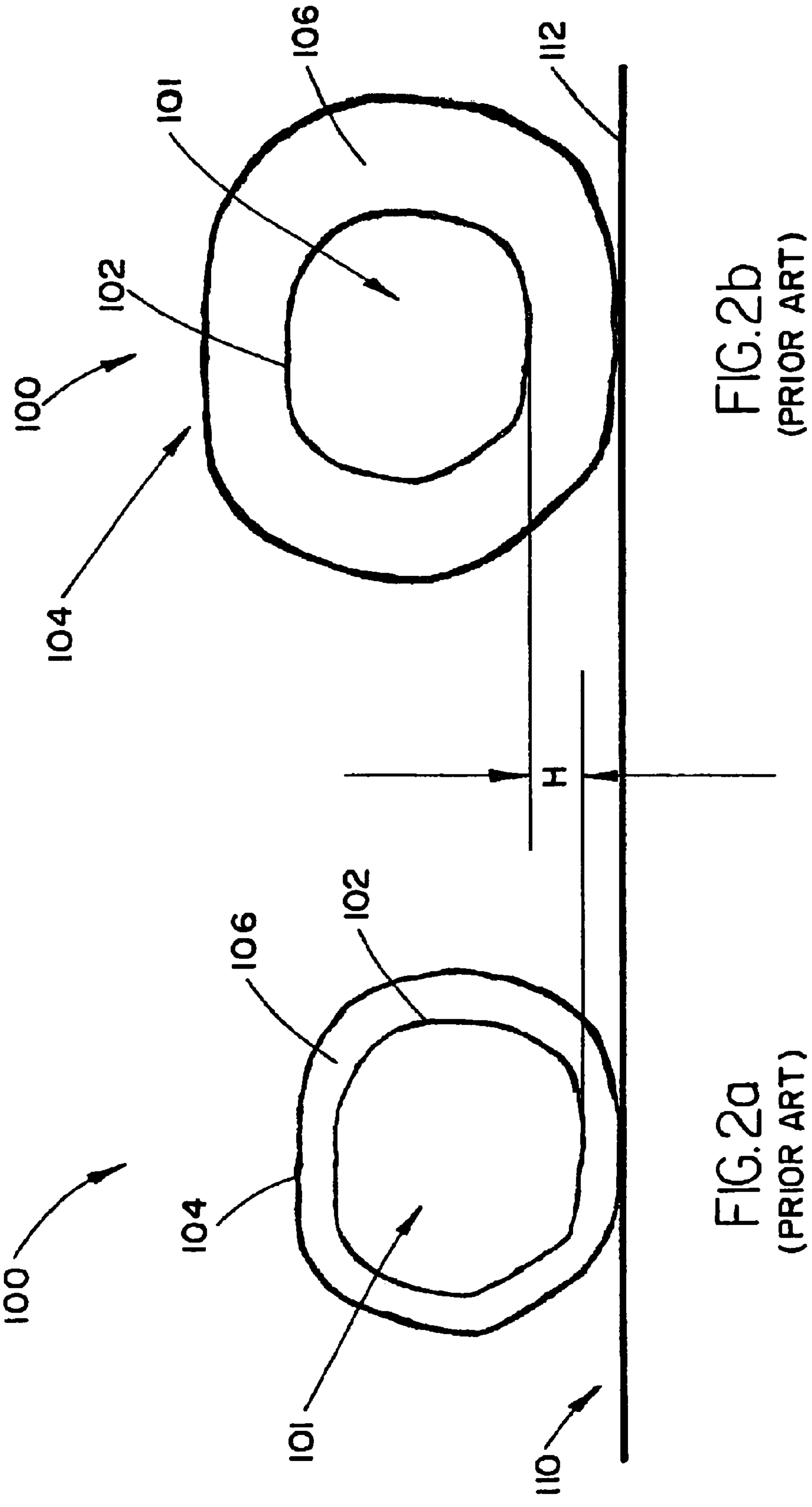
FIG.2b (PRIOR ART)
FIG.2a (PRIOR ART)
FIGS. 2*a* and 2*b* illustrate a comparison of the APPLICATOR of the prior art while undergoing a positive pressure cycle (FIG. 2*b*) and an evacuation cycle (FIG. 2*a*) thus showing a height H that a person's limb is lifted during the positive pressure cycle.
Figure 3A:
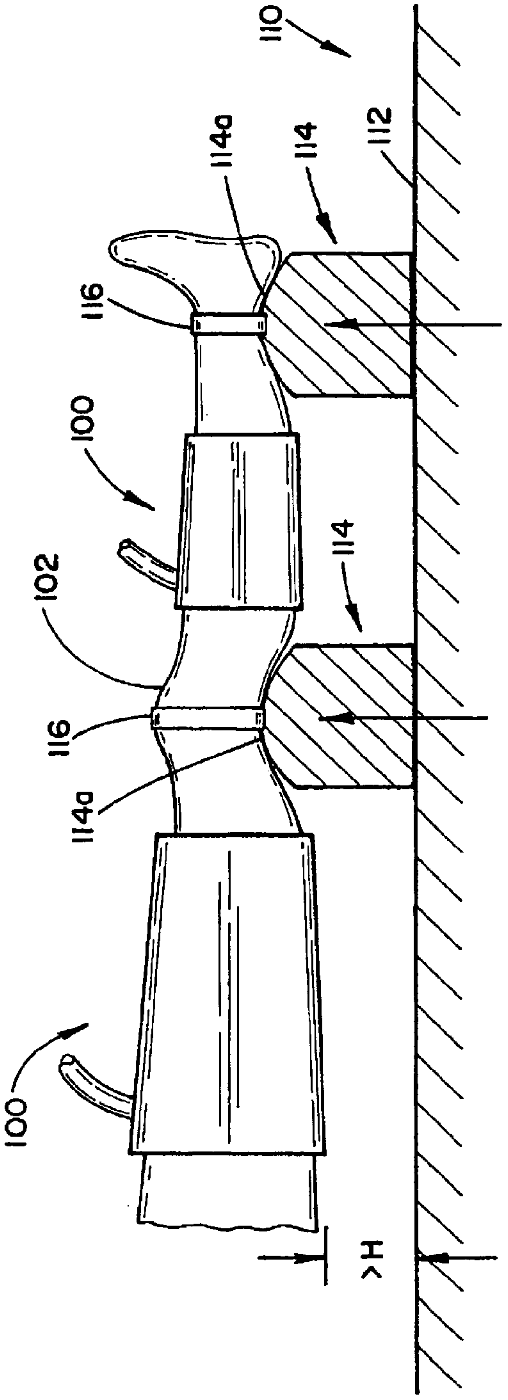
FIGS. 3*a* and 3*b* illustrate a side view and front view, respectively, of a first variation of the patient supports and table of the present invention.
Figure 3B:
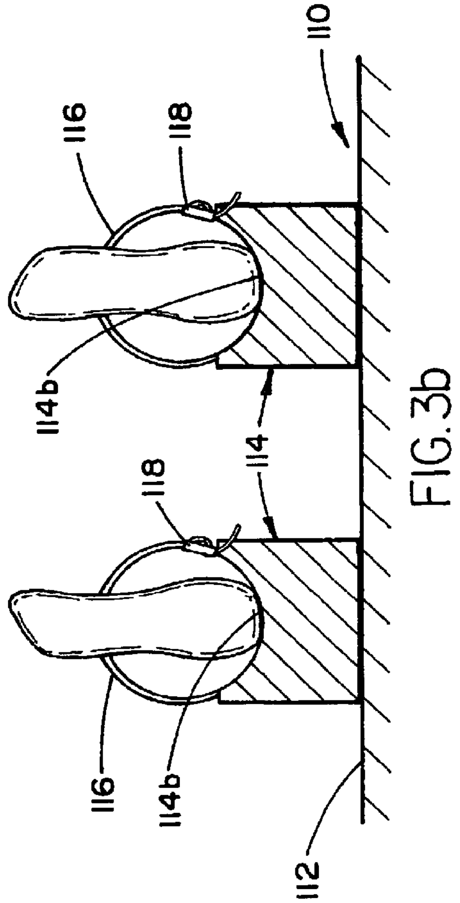

Referring now to FIGS. 3*a* and 3*b* a table having a tabletop 110 and a top surface 112 is shown. The tabletop is given by way of example only and not to limit the scope or spirit of the present invention. For example, the supports of the present invention are equally applicable to beds. Hereinafter, "table" and "tabletop" are collectively used to refer to tables, beds, and any other structure, such as a sling, which are used to support a patient in a lying or partially lying position. Although, the tabletop 110 is shown as not having any supporting structure, those skilled in the art will appreciate that the same can be supported by legs, a stand rails, or the like.

The patient support and table are particularly suited in external counterpulsation cardiac assist (ECPCAD) procedures for at least the reasons set forth above. The patient support comprises a base and at least one support 114 connected to the base for maintaining at least a portion of the patient above tabletop 110 during a positive pressure cycle of the external counterpulsation cardiac assist. Although, the base, in the preferred implementation, is a tabletop 110, as will be discussed below, the base does not have to be the tabletop, but can be positioned above the top surface 112 of the tabletop. Furthermore, the support 114 is described as being "connected" to the tabletop 110, however, such is intended to describe not only a fixation of the support on the tabletop 110 but also a placement of the support on the top surface 112 of the tabletop 110, as is shown in FIGS. 3*a* and 3*b*.

In the first embodiment of the present invention, as illustrated in FIGS. 3*a* and 3*b*, the supports 114 are provided under one or more of the exposed segments of the body, i.e., the feet, ankles, knees, back, neck and the head. The function of the supports 114 is to hold the limb/body above the top surface 112 of the tabletop 110, providing enough clearance to clear the inflated applicator's 100, thereby preventing the aforementioned up and down movement of the body/limb during the procedure. FIG. 3*a* illustrates two applicator's 100, a first positioned on the thigh and a second positioned on the shin. In this configuration, a first support 114 is positioned at the knee and a second support is supported at the ankle. It is assumed that the rest of the body is either supported on the tabletop 112 or on further supports (not shown). As is illustrated, in FIGS. 3*a* and 3*b*, the upper surface of the supports 114 are preferably curved to conform to the shape of the portion of the patient to be supported. The upper surface is preferably a complex curve. FIG. 3*a* shows surface 114*a* having a convexity to support the convexity of the joints while surface 114*b* has a concavity to conform to the cylindrical shape of the leg.

Preferably, the support surfaces 114*a*, 114*b* are made of sufficiently soft padded material and hold the limb or other body portion securely to prevent it from slipping off the supports 114. Although not preferred, a strap 116 and mating buckle 118 may be provided to retain the limb or other body portion on the support 114. The height of the supports 114 is sufficient to maintain the outer portions of the applicator 100 above the top surface 112 of the tabletop 110. In terms of the previously described prior art, the supports 114 should maintain the body portion to be supported above the top surface 112 of the tabletop 110 at a height greater than H.

Figure 4:
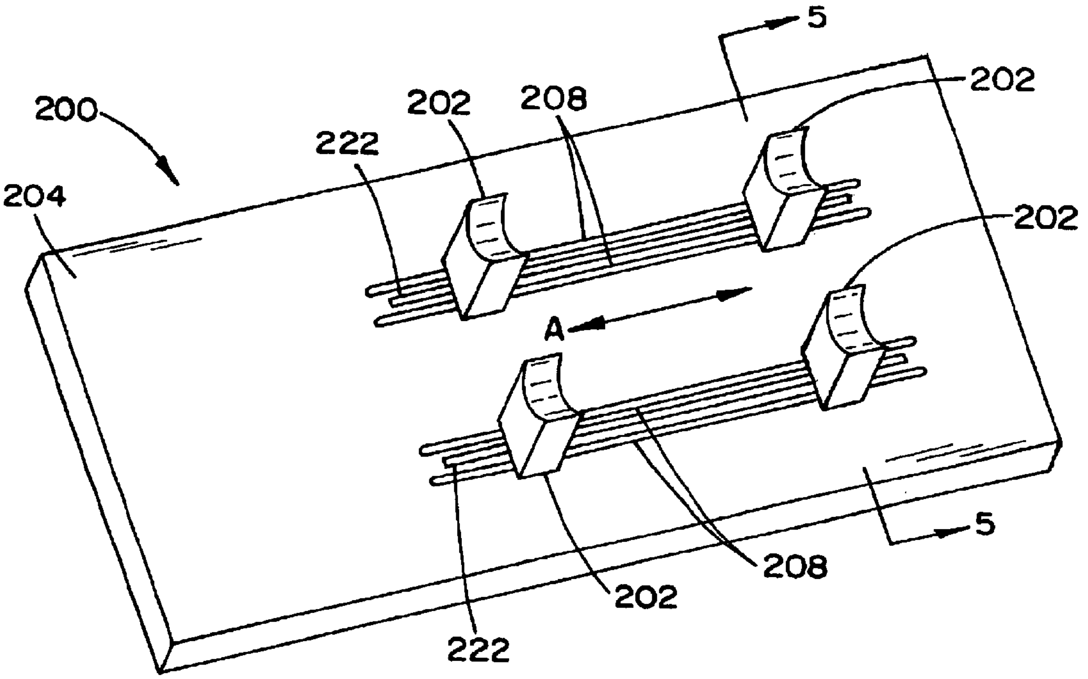
FIG. 4 illustrates an isometric view of another variation of the patient supports and table of the present invention.

Referring now to FIG. 4, there is shown a second embodiment of the present invention. In the second embodiment, the tabletop 200 has supports 202 having means for adjusting both the position of the supports 202 on the tabletop 200 and the height of the supports 202 above the top surface 204 of the tabletop 200. The means for adjusting the supports 202 under the body provides for the most comfortable height and positioning of the supports 202. Although the supports 202 are shown adjusting in a lateral direction (A), it will be appreciated by those skilled in the art that other directions of adjustment are possible and may be desired.

Figure 5:
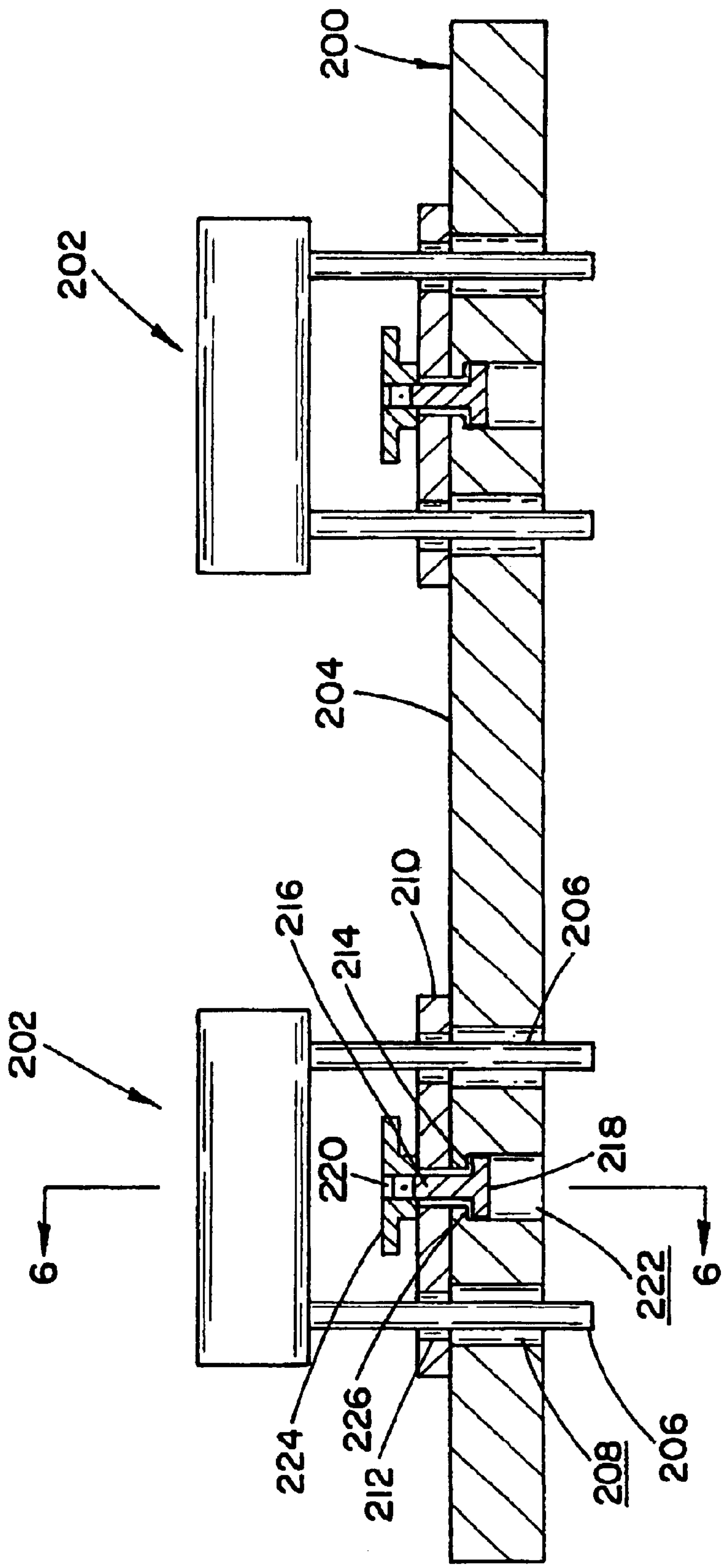
FIG. 5 illustrates a sectional view of the patient supports and table of FIG. 4 as taken along line 5—5 therein.

Referring now to FIG. 5, the means for movably fixing the supports 202 to the tabletop 200 is such that the supports 202 can be movably positioned under the portion of the patient to be maintained above the tabletop 200. The moving means preferably comprises the supports 202 having at least one, and preferably two slide portions 206, each of which are slidably arranged in a corresponding slot 208 on a top surface 204 of the tabletop 200. The slide portions 206 are preferably cylindrical shafts. The slots 206 are preferably arranged in the direction of adjustment along the tabletop 200, in the illustrated example, in the A direction. The slide portions 206 are prevented from falling into the slots 208 by a slide plate 210. The slide plate 210 is sized such that it has a larger dimension than the widest dimension of the slots 210 such that it slides on at least a portion of the top surface 204 of the tabletop 200. The slide plate 210 has bores 212 corresponding to each of the slide portions 206 and is either fixed therein to fix the height of the supports 202 above the top surface 204 of the tabletop 200, or as will be discussed below, the slide portions 206 can be movingly disposed in the bores 212 to provide a height adjustment of the supports 202.

The supports 202 preferably further have a locking means for locking the supports 202 at a predetermined position corresponding to the portion of the patient to be maintained above the tabletop 200. The locking means preferably comprises a locking shaft 214 disposed in a bore 216 of the slide plate 210. The locking shaft 214 has a keyed portion 218 on one end and a threaded portion 220 on another end. The keyed portion 218 is slidingly disposed in a corresponding keyway 222 in the tabletop 200. A threaded knob 224 is provided and is threadingly engaged with the threaded portion 220 of the locking shaft 214. When the threaded knob 224 is tightened on the locking shaft 214, the keyed portion 218 engages a lower surface 226 of the tabletop 200 to thereby lock the support 202 to the tabletop in a predetermined position along direction A.

Figure 6:
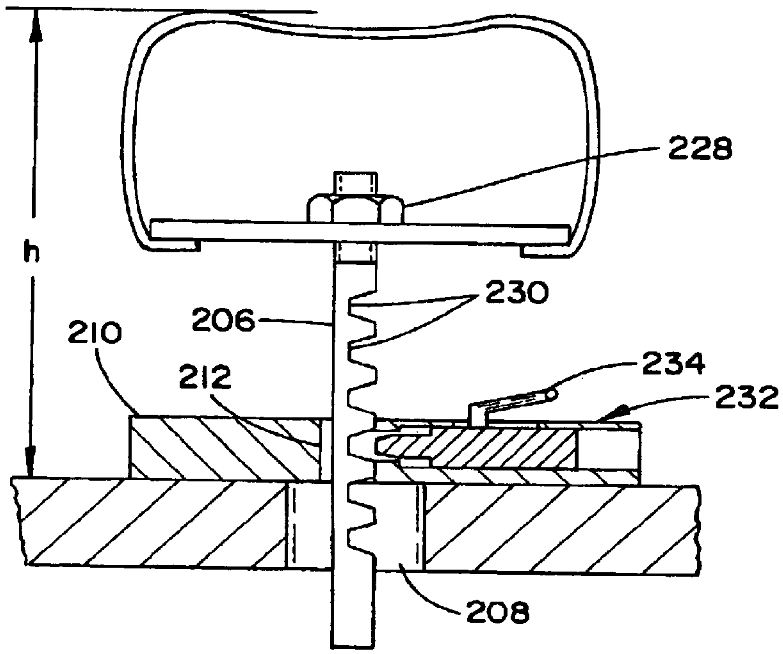
FIG. 6 illustrates a sectional view of the patient supports and table of FIG. 4 as taken along line 6—6 therein.

Referring now to FIG. 6, the tabletop further comprises a height adjustment means for movably fixing the support 202 to the tabletop 200 such that a height (h) of the supports above the top surface 204 of the tabletop 200 can be adjusted. The height adjustment means preferably comprises at least one rod, preferably the slide portions 206 connected to the support 202. The slide portions 206 being slidingly disposed in a corresponding bore 208 in the tabletop 200 and also in the bores 212 of the slide plate 210. The slide portions 206 preferably being connected to the support 202 by way of a threaded fastener 228.

A locking means is provided for locking the supports 202 at a predetermined height (h) above the top surface 204 of the tabletop 200. Preferably, the locking means comprises each of the slide portions 206 having at least one groove 230, and preferably a plurality of grooves 230 disposed along a length of the slide portions 206. A detent 232 is slidingly housed in either the tabletop 200 or preferably, the slide plate 210 for operatively engaging and disengaging with the grooves 230. A release means, such as handle 234 pulls the detent from the groove 230 to release the detent 232 from the groove 230 and allow adjustment of the height of the support 202. Such release means are well known in the art, particularly in the art of automobile headrests. After release of the detent 232 the support 202 can be raised or lowered such that the detent 232 aligns with another groove 230 corresponding to a desired height. After such, the handle 234 is pushed forward to engage the desired groove 230 and thereby lock the support 202 at a desired height. Although the release means is shown as being manually operated, automatic release means can also be employed.

Figure 7:
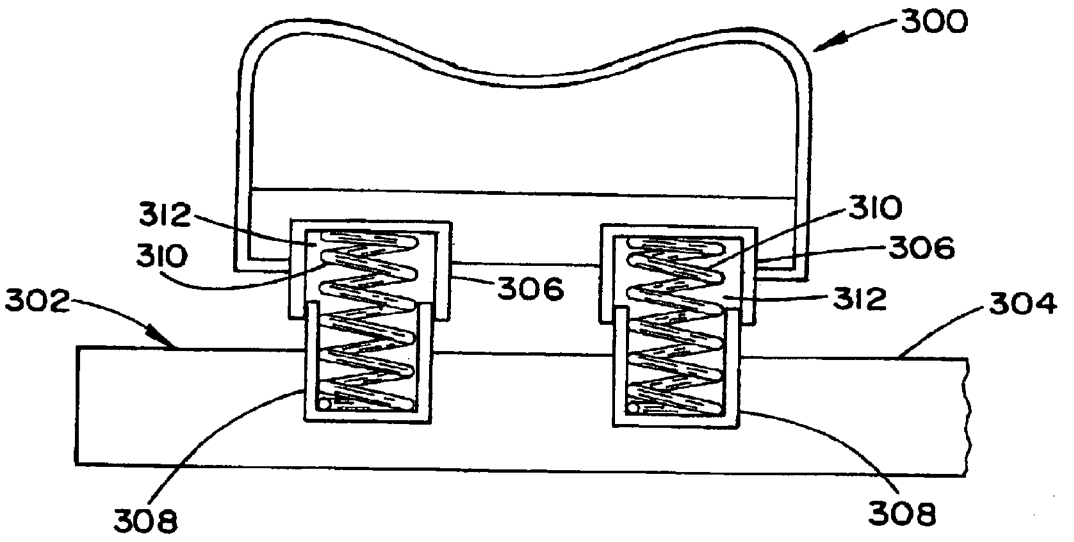
FIG. 7 illustrates yet another variation of the patients support and table of the present invention.

Referring now to FIG. 7, there is illustrated another version of the supports 300 for supporting a patient above a top surface 304 of a tabletop 302. Supports 300 being similar to the previously described supports 114, 202 but has a biasing means for biasing the support 300 above the tabletop 302. The biasing means preferably comprises a first cupped collar 306 disposed in the support 300 and a second cupped collar 308 disposed in the tabletop 302. The second cupped collar 308 further having a portion slidingly disposed in the first cupped collar 306. Preferably a pair of the first and second cupped collars 306, 308 are provided. A constant tension biasing spring 310 is disposed in a cavity 312 defined by the first and second cupped collars 306, 308 to bias the support 300 away from the top surface 304 of the tabletop 302.

Figure 10:
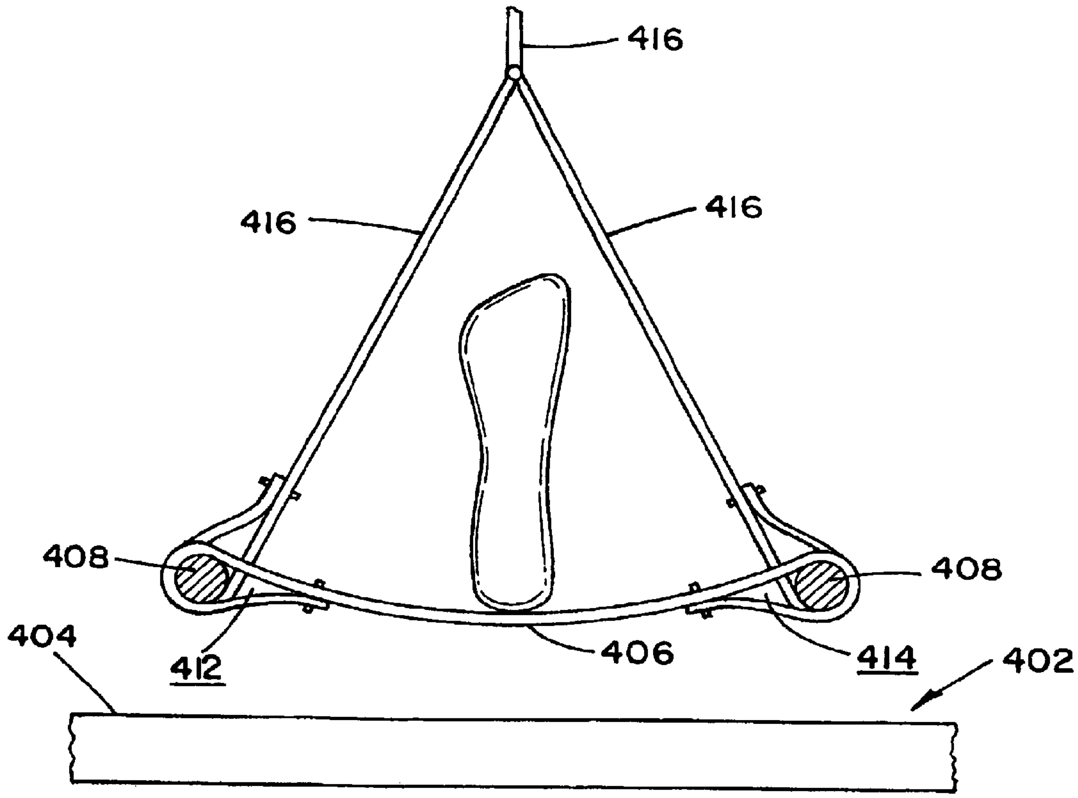
FIG. 10 illustrates a partial front view of the implementations of the patient supports and table of FIGS. 8 and 9.
Figure 8:
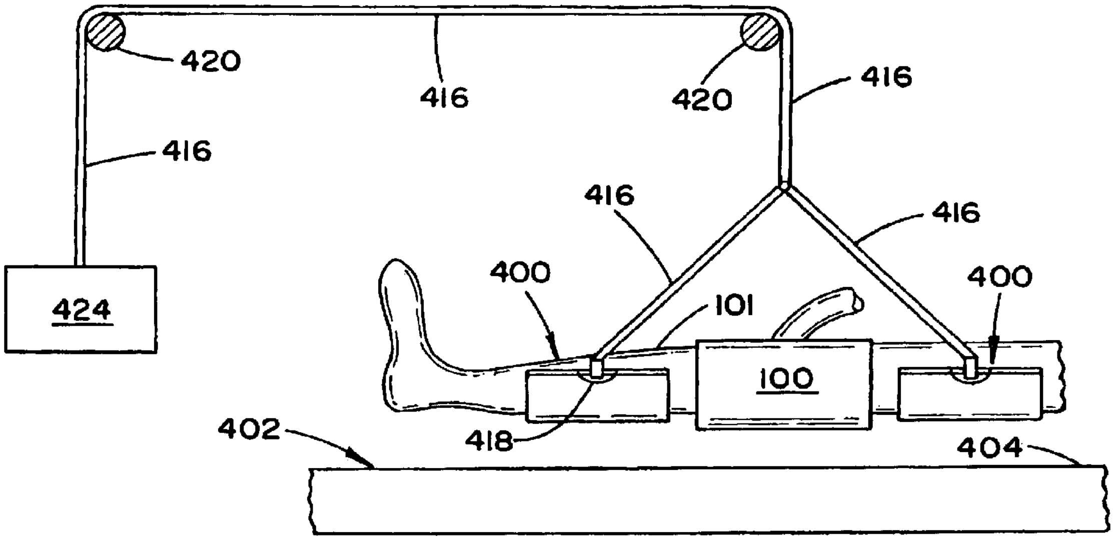
FIG. 8 illustrates a preferred implementation of still yet another variation of the patient supports and table of the present invention.
Figure 9:
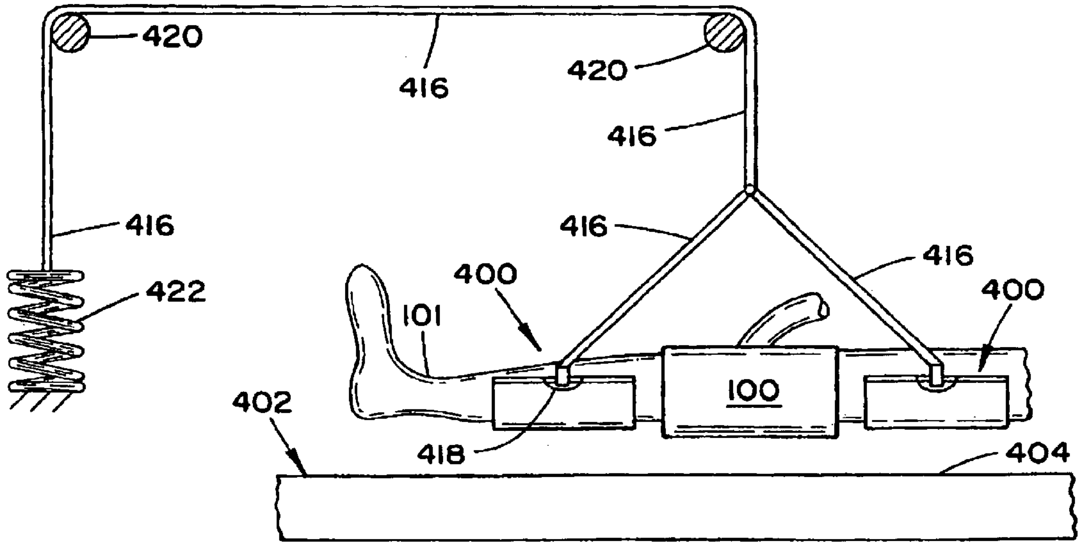
FIG. 9 illustrates an alternative implementation of the patient supports and table of FIG. 8.

Referring now to FIGS. 8–10, there is shown another embodiment of the present invention where the base is raised above the level of the patient and the top surface 404 of the tabletop 402 and one or more of supports 400 hold the limb sufficiently above the bed surface by an overhanging support, i.e., by placing the exposed segment (e.g., foot, ankle, knee, etc.) into a sling type of support 400 to support the limb/body above the top surface 404 of the tabletop 402, providing enough clearance to clear the inflated Applicator's 100. Preferably more than one sling is provided, strategically positioned about the APPLICATOR 100.

The support 400 preferably comprises a sling portion 406 and first and second sling bars 408, 410. The sling portion preferably being a fabric such as canvas and having first and second loops 412, 414 in which the first and second sling bars are disposed. The support 400 further has a tensioning member, such as a cable 416. The cable 416 being attached to the sling rods 408, 410 at a first end. Preferably, an end of the cable 416 is looped around each of the sling bars 408, 410 and clamped as is known in the art. A hole 418 is provided in the sling portion 406 to accommodate the fastening of the cable 416 to the sling rods 408, 410.

The cable 416 is routed over at least one, and preferably two pulleys 420 connected to the ceiling or other structure. The cable 416 is connected at another end to a balancing means for maintaining the support 400 in a balanced position to maintain the patient above the tabletop 402. In a first variation shown in FIG. 9, the balancing means is a constant tension spring 422 attached at one end to the cable 416 and at another end to the floor or other structure. In a second variation shown in FIG. 8, the balancing means is a counterweight 424 attached to the cable 416, such that the counterweight 424 hangs freely from the cable 416.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A patient support for an external counterpulsation cardiac assist procedure, the patient support comprising:

a base, wherein the base is the tabletop;

at least one support connected to the tabletop for maintaining at least a portion of the patient above the tabletop during a positive pressure portion of the external counterpulsation cardiac assist procedure; and moving means for movably fixing the at least one support to the tabletop such that the at least one support can be movably positioned under the portion of the patient to be maintained above the tabletop, wherein the moving means comprises the at least one support having a slide portion which is slidably arranged in a corresponding slot on a top surface of the tabletop;

wherein the at least one support further having a locking means for locking the at least one support at a predetermined position corresponding to the portion of the patient to be maintained above the tabletop;

wherein the locking means comprises a locking shaft having a keyed portion on one end and a threaded portion on another end, the keyed portion being slidingly disposed in a corresponding keyway in the tabletop, the locking means further comprising a threaded knob threadingly engaged with the threaded portion, wherein tightening of the knob on the shaft causes the keyed portion to engage a lower surface of the tabletop to thereby lock the at least one support thereon.

2. The patient support of claim 1, wherein the at least one support comprises a padded portion fabricated of a soft material.

3. The patient support of claim 2, wherein the at least one support further comprises a fixing means for fixing the at least a portion of the patient thereto.

4. The patient support of claim 3, wherein the fixing means comprises a strap having a first end fixed to the at least one support and a corresponding buckle fixed to the at least one support.

5. The patient support of claim 1, wherein the base is the tabletop.

6. The patient support of claim 5, further comprising height adjustment means for movably fixing the at least one support to the tabletop such that a height of the at least one support above the tabletop can be adjusted.

7. The patient support of claim 6, wherein the height adjustment means comprises at least one rod connected to the at least one support, the at least one rod being slidingly disposed in a corresponding bore in the tabletop.

8. The patient support of claim 7, further comprising a locking means for locking the rod at a predetermined height, wherein the locking means comprises the at least one rod having at least one groove and a detent housed in the tabletop for operatively engaging with the at least one groove.

9. The patient support of claim 1, further comprising biasing means for biasing the at least one support above the tabletop.

10. The patient support of claim 9, wherein the biasing means comprises a constant tension spring corresponding to each of the at least one supports, the constant tension spring having a portion disposed in the tabletop and a portion connected to the at least one support.

11. The patient support of claim 1, wherein the base is raised above the level of the patient and tabletop.

12. The patient support of claim 11, wherein the at least one support comprises a sling, the sling having a tensioning member and balancing means for maintaining the sling in a balanced position to maintain the at least a portion of the patient above the tabletop.

13. The patient support of claim 12, wherein the tensioning member is a cable attached at a first end to the sling and at a second end to the balancing means.

14. The patient support of claim 12, wherein the balancing means is a constant tension spring attached to the second end.

15. The patient support of claim 12, wherein the balancing means is a counterweight attached to the second end.

16. A patient table for use with an external counterpulsation cardiac assist procedure, the patient table comprising:

a tabletop having a top surface;

at least one support connected to the tabletop for maintaining at least a portion of the patient above the top surface of the tabletop during a positive pressure portion of the external counterpulsation cardiac assist procedure; and moving means for movably fixing the at least one support to the tabletop such that the at least one support can be movably positioned under the portion of the patient to be maintained above the tabletop, wherein the moving means comprises the at least one support having a slide portion which is slidably arranged in a corresponding slot on the top surface of the tabletop;

wherein the at least one support further having a locking means for locking the at least one support at a predetermined position corresponding to the portion of the patient to be maintained above the tabletop;

wherein the locking means comprises a locking shaft having a keyed portion on one end and a threaded portion on another end, the keyed portion being slidingly disposed in a corresponding keyway in the tabletop, the locking means further comprising a threaded knob threadingly engaged with the threaded portion, wherein tightening of the knob on the shaft causes the keyed portion to engage a lower surface of the tabletop to thereby lock the at least one support thereon.

17. The patient table of claim 16, wherein the at least one support comprises a padded portion fabricated of a soft material.

18. The patient table of claim 17, wherein the at least one support further comprises a fixing means for fixing the at least a portion of the patient thereto.

19. The patient table of claim 18, wherein the fixing means comprises a strap having a first end fixed to the at least one support and a corresponding buckle fixed to the at least one support.

20. A patient table, for use with an external counterpulsation cardiac assist procedure, the patient table comprising:

a tabletop having a top surface;

at least one support connected to the tabletop for maintaining at least a portion of the patient above the top surface of the tabletop during a positive pressure portion of the external counterpulsation cardiac assist procedure; and height adjustment means for movably fixing the at least one support to the tabletop such that a height of the at least one support above the tabletop can be adjusted;

wherein the height adjustment means comprises at least one rod connected to the at least one support, the at least one rod being slidingly disposed in a corresponding bore in the tabletop.

21. The patient table of claim 20, further comprising a locking means for locking the rod at a predetermined height, wherein the locking means comprises the at least one rod having at least one groove and a detent housed in the tabletop for operatively engaging with the at least one groove.

22. The patient table of claim 16, further comprising biasing means for biasing the at least one support above the top surface of the tabletop.

23. The patient table of clam 22, wherein the biasing means comprises a constant tension spring corresponding to each of the at least one supports, the constant tension spring having a portion disposed in the tabletop and a portion connected to the at least one support.

* * * * *